United States Patent [19]
Crawford et al.

[11] Patent Number: 5,601,536
[45] Date of Patent: Feb. 11, 1997

[54] NEEDLE TIP COVER

[75] Inventors: Mark A. Crawford, Sandy; Timothy J. Erskine; Gerald H. Peterson, both of Salt Lake City, all of Utah

[73] Assignee: Becton Dickinson and Company, Franklin Lakes, N.J.

[21] Appl. No.: 463,618

[22] Filed: Jun. 5, 1995

Related U.S. Application Data

[62] Division of Ser. No. 364,071, Dec. 27, 1994, Pat. No. 5,558,651, which is a continuation of Ser. No. 114,988, Aug. 12, 1993, abandoned, which is a continuation of Ser. No. 512,284, Apr. 20, 1990, abandoned.

[51] Int. Cl.[6] .................................................. A61M 5/00
[52] U.S. Cl. ......................... 604/263; 604/166; 604/198
[58] Field of Search ................................... 604/110, 162, 604/164, 166, 167, 168, 192, 197, 198, 263, 53, 272; 128/919

[56] References Cited

U.S. PATENT DOCUMENTS

| | | |
|---|---|---|
| 2,876,770 | 3/1959 | White . |
| 3,008,570 | 11/1961 | Roehr et al. . |
| 3,052,241 | 9/1962 | Myerson et al. . |
| 3,134,380 | 5/1964 | Armao . |
| 3,354,881 | 11/1967 | Bloch . |
| 3,370,588 | 2/1968 | Burke . |
| 3,401,693 | 9/1968 | Cohen . |
| 3,468,309 | 9/1969 | Drewe . |
| 3,884,230 | 5/1975 | Wulff . |
| 3,904,033 | 9/1975 | Haerr . |
| 4,139,009 | 2/1979 | Alvarez . |
| 4,237,882 | 12/1980 | Wickham . |
| 4,356,822 | 11/1982 | Winstead-Hall . |
| 4,425,120 | 1/1984 | Sampson et al. ............... 604/198 |
| 4,553,962 | 11/1985 | Brunet ............................. 604/198 |
| 4,573,981 | 3/1986 | McFarlane ...................... 604/263 |
| 4,610,671 | 9/1986 | Luther ............................. 604/168 |
| 4,631,057 | 12/1986 | Mitchell .......................... 604/198 |
| 4,634,428 | 1/1987 | Cuu ................................. 604/110 |
| 4,643,722 | 2/1987 | Smith, Jr. ........................ 604/192 |
| 4,650,468 | 3/1987 | Jennings, Jr. ................... 604/110 |
| 4,659,330 | 4/1987 | Nelson et al. .................. 604/192 |
| 4,660,570 | 4/1987 | Dombrowski ................... 128/765 |
| 4,664,259 | 5/1987 | Landis . |
| 4,664,653 | 5/1987 | Sagstetter et al. .............. 604/197 |
| 4,675,005 | 6/1987 | Deluccia ......................... 604/110 |
| 4,693,708 | 9/1987 | Wanderer et al. .............. 604/198 |
| 4,695,274 | 9/1987 | Fox .................................. 604/198 |
| 4,723,943 | 2/1988 | Spencer .......................... 604/198 |
| 4,725,267 | 2/1988 | Vaillancourt ................... 604/192 |
| 4,731,059 | 3/1988 | Wanderer et al. .............. 604/192 |
| 4,735,618 | 4/1988 | Hagen ............................. 604/192 |
| 4,740,205 | 4/1988 | Seltzer et al. .................. 604/192 |
| 4,743,233 | 5/1988 | Schneider ....................... 604/192 |
| 4,755,170 | 7/1988 | Golden ............................ 604/52 |
| 4,762,516 | 8/1988 | Luther et al. ................... 604/164 |
| 4,772,272 | 9/1988 | McFarland ...................... 604/198 |
| 4,775,367 | 10/1988 | Schmidt .......................... 604/192 |
| 4,775,369 | 10/1988 | Schwartz ........................ 604/263 |
| 4,846,804 | 7/1989 | Davis et al. .................... 604/164 |
| 4,846,805 | 7/1989 | Sitar ................................ 604/165 |
| 4,850,961 | 7/1989 | Wanderer et al. .............. 604/53 |

(List continued on next page.)

FOREIGN PATENT DOCUMENTS 0344606  12/1989  European Pat. Off. .

*Primary Examiner*—Randall L. Green
*Assistant Examiner*—V. Alexander
*Attorney, Agent, or Firm*—Eric M. Lee, Esq.

[57] ABSTRACT

A needle and a cover with a needle having an elongate shank and a tip with a sharpened point. The cover is coaxially associated with the elongate shank for movement therealong toward the tip and includes a part for extending beyond the sharpened point when the cover is positioned near the tip. A lock associated with the needle and cover cooperates with and holds the cover to prevent axial movement relative to the needle tip after positioning the cover near the tip. A retaining member on the adapter and on the cover releasably attach the cover to the adapter while on the elongate shank of the needle allowing the needle and cover to be disengaged from the catheter and adapter after placement.

5 Claims, 9 Drawing Sheets

U.S. PATENT DOCUMENTS

| | | | |
|---|---|---|---|
| 4,850,977 | 7/1989 | Bayless | 604/198 |
| 4,904,244 | 2/1990 | Harsh et al. | 604/187 |
| 4,911,694 | 3/1990 | Dolan | 604/198 |
| 4,929,241 | 5/1990 | Kulli | 604/263 |
| 4,935,012 | 6/1990 | Magre et al. | 604/192 |
| 4,952,207 | 8/1990 | Lemieux | 604/164 |
| 4,955,866 | 9/1990 | Corey | 604/192 |
| 4,964,854 | 10/1990 | Luther | 607/166 |
| 4,973,317 | 11/1990 | Bobrove | 604/198 |
| 4,990,141 | 2/1991 | Byrne et al. | 604/198 |
| 4,994,041 | 2/1991 | Dombrowski et al. | 604/164 |
| 5,015,242 | 5/1991 | Heifetz | 604/198 |
| 5,049,136 | 9/1991 | Johnson | 604/198 |
| 5,051,109 | 9/1991 | Simon | 604/263 |
| 5,053,017 | 10/1991 | Chamuel | 604/192 |
| 5,059,180 | 10/1991 | McLees | 604/110 |
| 5,059,184 | 10/1991 | Dyke | 604/198 |
| 5,135,504 | 8/1992 | McLees | 604/164 |
| 5,135,505 | 8/1992 | Kaufman | 604/165 |
| 5,169,391 | 12/1992 | Vogel | 604/177 |
| 5,176,655 | 1/1993 | McCormick et al. | 604/198 |
| 5,183,468 | 2/1993 | McLees | 604/164 |
| 5,215,528 | 6/1993 | Purdy et al. | 604/164 |
| 5,328,482 | 7/1994 | Sircom et al. | 604/164 |

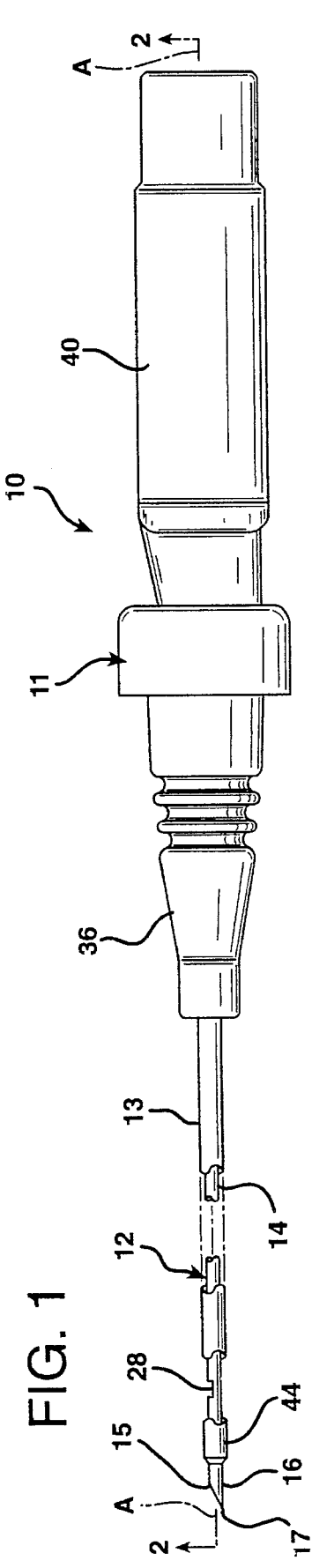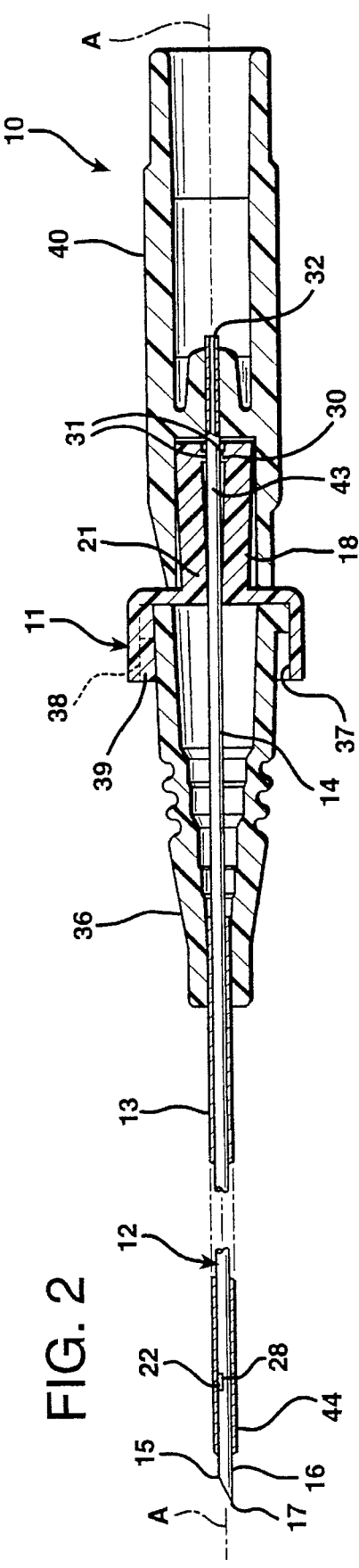

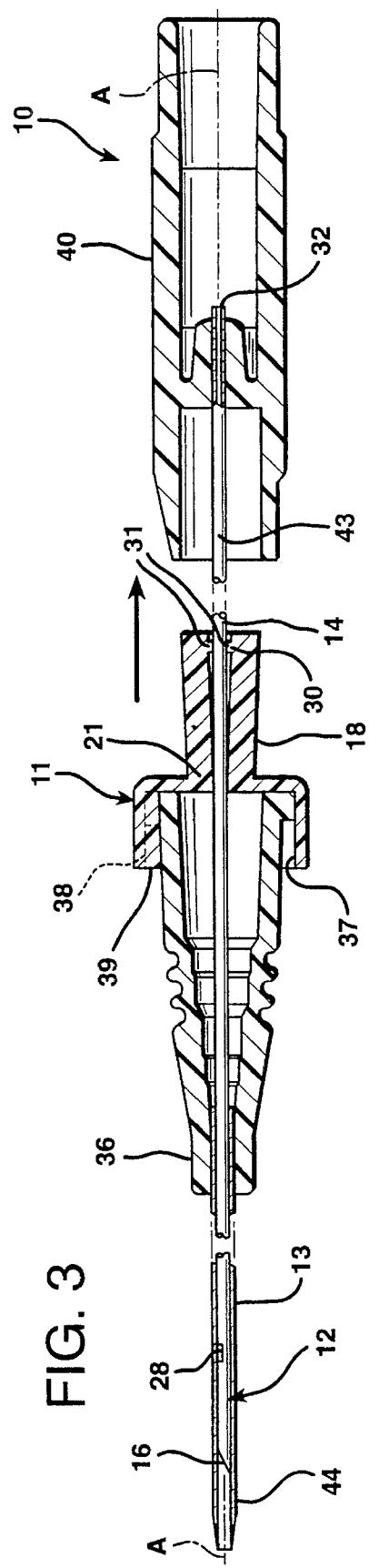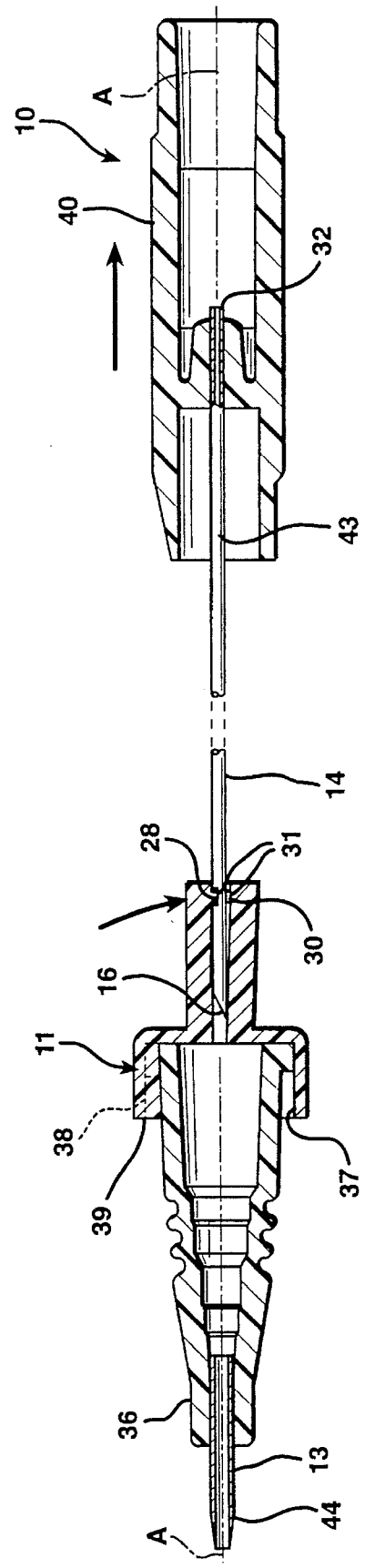

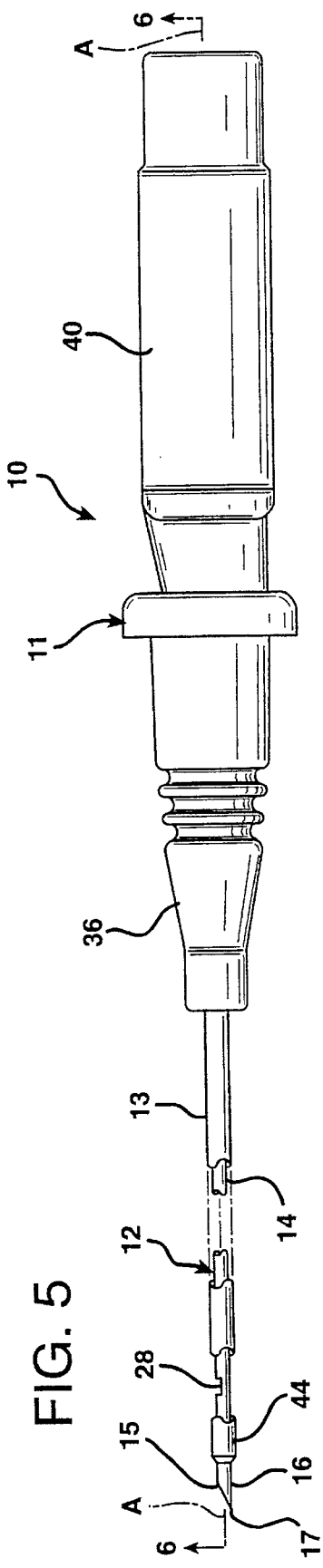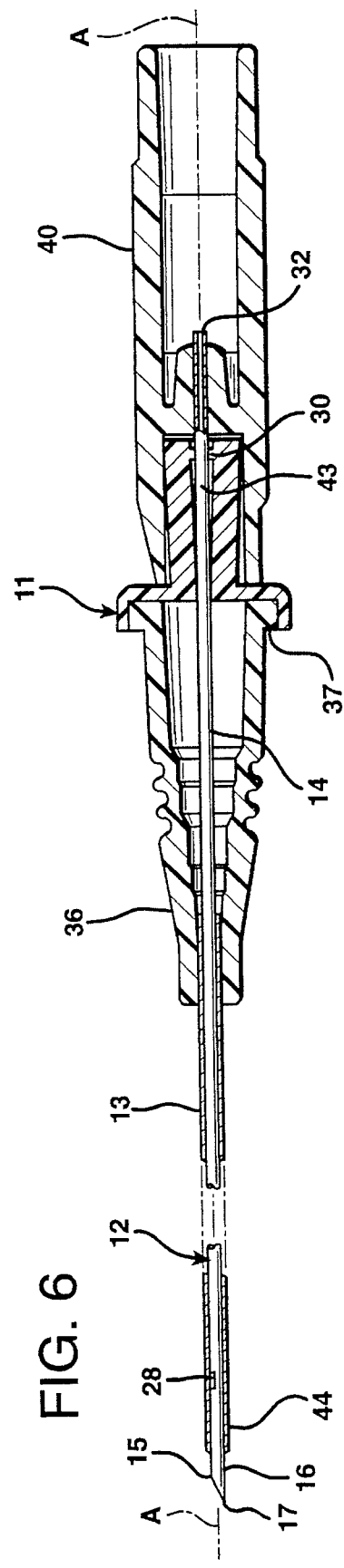
FIG. 5
FIG. 6

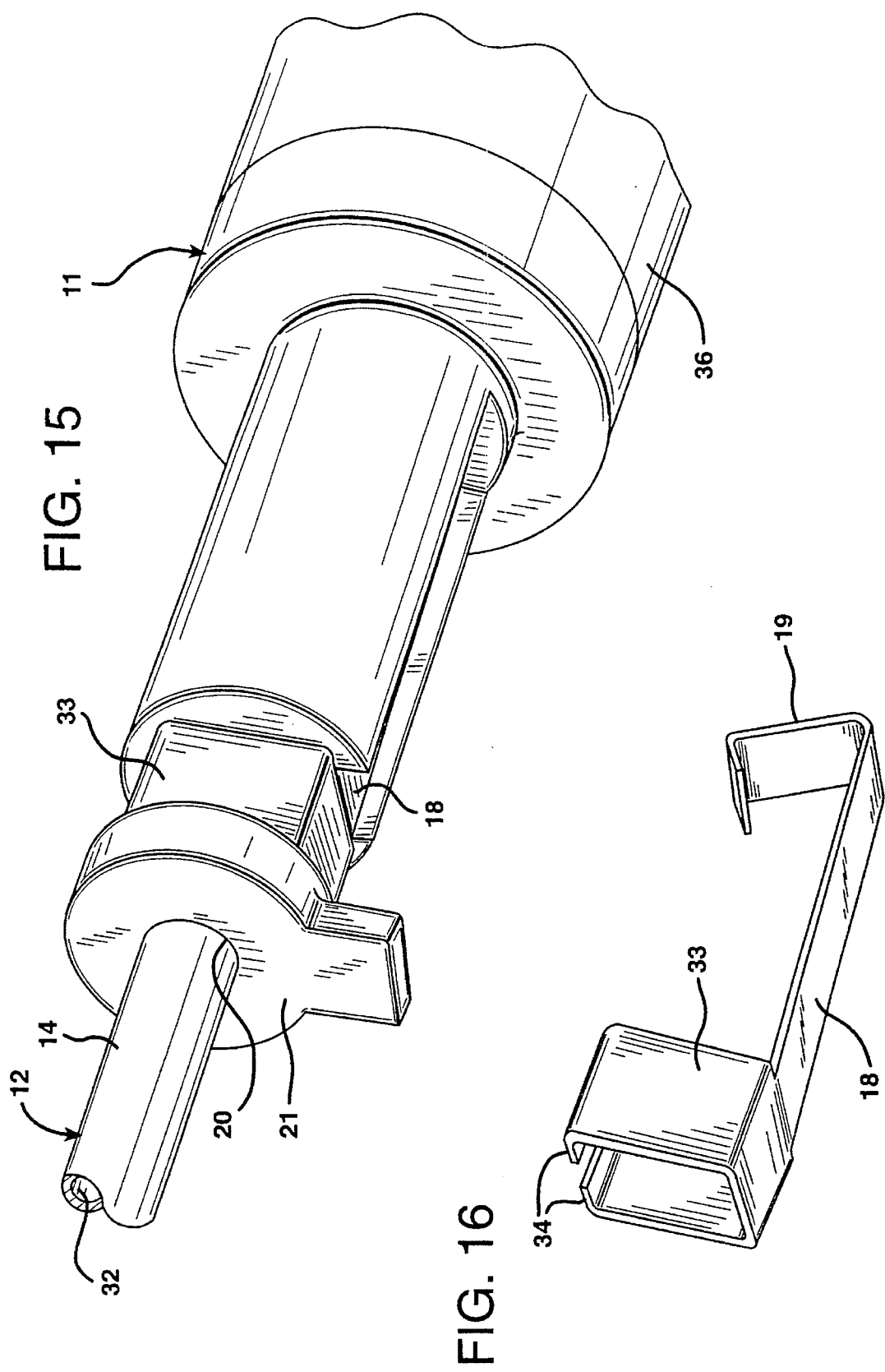

NEEDLE TIP COVER

This application is a division of patent application Ser. No. 08/364,071 filed Dec. 27, 1994, now U.S. Pat. No. 5,558,691, which is a continuation of patent application Ser. No. 08/114,988 filed Aug. 12, 1993, now abandoned, which is a continuation of patent application Ser. No. 07/512,284 filed Apr. 20, 1990, now abandoned.

FIELD OF THE INVENTION

This invention relates to a needle tip cover to prevent transmission of infection and more particularly, relates to a tip cover for locking about the tip of a disposable needle after use to prevent accidental delivery of infectious organisms by penetration of the used needle tip into an animal.

BACKGROUND OF THE INVENTION

With concern about infection, transmission of AIDS, hepatitis and similar incurable diseases of the blood, methods and devices to enclose the used disposable needle tip have become very important and in great demand. Many approaches to guard the needle, protect users and/or otherwise prevent injury have been proposed. All of them are cumbersome, expensive and interfere with the normal and accepted procedure for the insertion of an over the needle catheter. Typical of such introducers is U.S. Pat. No. 4,846,805 wherein the shield slides over the flash chamber body to engage the catheter and lock about the used needle tip.

Specifically, after the catheter has been inserted by an over the needle procedure and blood flashback has been observed, the catheter is advanced and/or the needle is withdrawn. After the catheter is inserted into the vessel as desired and the needle is withdrawn and discarded, protection of the used needle tip becomes important. Needle guards are of three types which either hide the withdrawn needle within the needle carrying hub, require replacement of a separate needle guard or include a sliding shield which can be positioned distally over the used needle. Some of these types of guards lock to secure the guard in the needle protecting position thereby preventing injury.

Those needle guards are cumbersome and interfere with the single hand over the needle catheter placement procedure as disclosed in Stanley, U.S. Pat. No. 3,714,945. The needle tip cover disclosed herein does not interfere with or require any additional steps, procedures or cumbersome mechanisms which interfere with the accepted over the needle technique.

U.S. Pat. No. 3,134,380 has a needle shield for a hypodermic needle and that needle shield is not provided to prevent infection but is included to preserve sterility and to hide the needle prior to use. The device therein includes a compressible resilient sleeve which is carried on the distal end of a syringe barrel to extend outwardly therefrom over the needle and its tip. The sleeve is axially collapsible during placement of the needle in the vessel and reextends due to the resilience of the sleeve as the needle is extracted from the vessel. The distal end of the sleeve is arranged to be carried about the needle and in its extended position rests beyond the tip. No means of locking the sleeve in the extended position is disclosed.

U.S. Pat. No. 4,846,804 has a needle tip protector with a collapsible sleeve disposed about the shank of the needle and a protective cap located at the distal end thereof. The cap surrounds and encloses the tip of the needle. A sealing member is located within the cap to enclose the tip until the needle is pushed through the sealing member. Similarly, U.S. Pat. No. 3,354,881 has a compressible device extending over the needle shank. Rubber septa are provided at the opposite ends of the compressible device so as to surround the needle.

U.S. Pat. No. 4,139,009 has a needle tip protector with a permanently attached cover surrounding the needle and a number of elastic arms which extend along the length of the needle. The arms are constructed so as to bow outwardly from the needle shank when the needle is pressed against and into the patient. U.S. Pat. No. 4,660,570 shows a needle tip protector with a membrane extending over the sharp point of the needle whereby penetration causes the needle to extend through the membrane and the skin of the patient.

U.S. Pat. No. 4,650,468 has a device with a sleeve concentrically placed about the needle shank. A safety shield at one end has a rubber membrane extending across an opening in the shield. The membrane is adapted to be pierced by the needle tip for use.

SUMMARY OF THE INVENTION

The invention most preferably is a needle and cover for use with a needle having an elongate shank relative to an axis thereof. The needle has a tip at one axial end with a sharpened point. The cover is coaxially associated with the elongate shank for sliding movement therealong toward the tip. The cover includes a part for extending along the axis beyond the sharpened point when the cover is positioned near the tip. A lock associated with the needle and the cover cooperates and holds the cover to prevent axial movement of the cover relative to the needle tip after the cover is positioned distally along the elongate shank near the tip with the part that extends over the sharpened point.

The cover may have a bearing for circumscribing and guiding during coaxial sliding on the elongate shank. The part which extends hangs cantilever off the bearing to extend beyond the sharpened point preventing accidental injury. The lock may have a change in contour of the needle near where the elongate shank joins the tip so when the cover interengages with the change in contour it becomes locked relative to the needle preventing further axial movement.

The bearing has an inside diameter which most preferably rides upon the shank for axial movement therealong and the bearing is such that engagement with the change in contour prevents distal travel. The part which extends controls the proximal axial movement of the cover up the elongate shank away from the tip after thus locking the cover near the tip.

The change of contour may be a transition between a reduced diameter of the elongate shank and an enlarged diameter of the tip, a roughened surface on the needle, a change in cross section from a circular cross section for the elongate shank to a non-circular cross section near the tip or a notch which extends into the needle providing a latch face for a pawl on the cover.

The invention may be a part of a catheter assembly having a catheter and an adapter connected to one another for fluid communication and carried coaxially about a needle and hub. The catheter has a bore therethrough sized to surround the elongate shank of the needle for movement therewith during insertion and therealong during placement. A retaining means on the adapter and on the cover may releasably attach the cover to the adapter while the catheter and adapter are on the elongate shank of the needle. The retaining means permit the needle and cover to be disengaged from the catheter and adapter after placement of the catheter in the vessel. The lock cooperates and secures the cover to prevent the cover from axial movement relative to the needle tip after the cover is positioned near the tip.

The invention further includes a method of assembly of the hub and cover to the needle. The steps of placing the cover coaxially about the elongate shank with the bearing thereof axially slidable therealong toward the tip and securing the hub to the end of the elongate shank over which the bearing was placed thereby capturing the cover between the tip and the hub.

A method of inserting the over the needle catheter assembly is a part of the invention. The preferred method has the steps of applying pressure to the catheter assembly to penetrate the skin of the animal with the tip of the needle and carry the distal part of the coaxially positioned catheter into the body, inserting the catheter further with an over the needle procedure by holding the hub thereof between a finger and the thumb of the user and moving the cover axially along the needle from the hub to the tip with another finger while withdrawing the hub and needle from the inserted catheter and adapter with the other finger and thumb.

BRIEF DESCRIPTION OF THE DRAWINGS

FIG. 1 is a side view of a catheter assembly with a needle tip cover on the needle shank between the catheter adapter and the needle hub and wherein the needle is fully seated within the catheter.

FIG. 2 is a view of the needle tip cover of FIG. 1 shown in a cross section taken along line 2—2 of FIG. 1, FIG. 3 is a view of the needle tip cover of FIG. 1 shown in cross section as in FIG. 2 except the needle is shown partially withdrawn from the catheter.

FIG. 4 is a view of the needle tip cover of FIG. 1 shown in cross section as in FIGS. 2 and 3 except the needle is shown mostly withdrawn from the catheter.

FIG. 5 is a side view of a catheter assembly of an alternate needle tip cover located between the needle hub and the catheter adapter and wherein the needle is fully seated within the catheter.

FIG. 6 is a view of the alternate needle tip cover of FIG. 4 shown in cross section.

FIG. 15 is a perspective view showing the tip cover and the metal spring and how they fit one another forming a cover for a needle tip.

FIG. 16 is a perspective view of the metal spring used in connection with the tip cover of FIGS. 13, 14 and 15.

DETAILED DESCRIPTION OF THE INVENTION

Figure 7:
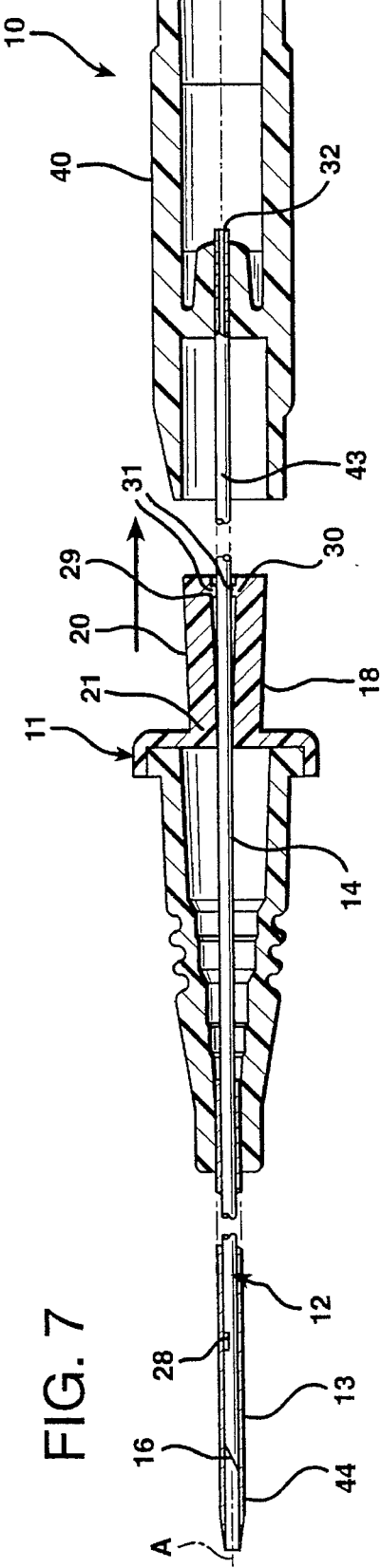
FIG. 7 is a view of the alternate needle tip cover of FIG. 4 shown in cross-section as in FIG. 6 except the needle is shown partially withdrawn from the catheter.

While this invention is satisfied by embodiments in many different forms, there is shown in the drawings and will herein be described in detail, a preferred embodiment and alternate embodiments of the invention, with the understanding that the present disclosure is to be considered as exemplary of the principles of the invention and is not intended to limit the invention to any one of the embodiments illustrated. The scope of the invention will be measured by the appended claims and their equivalents.

Figure 8:
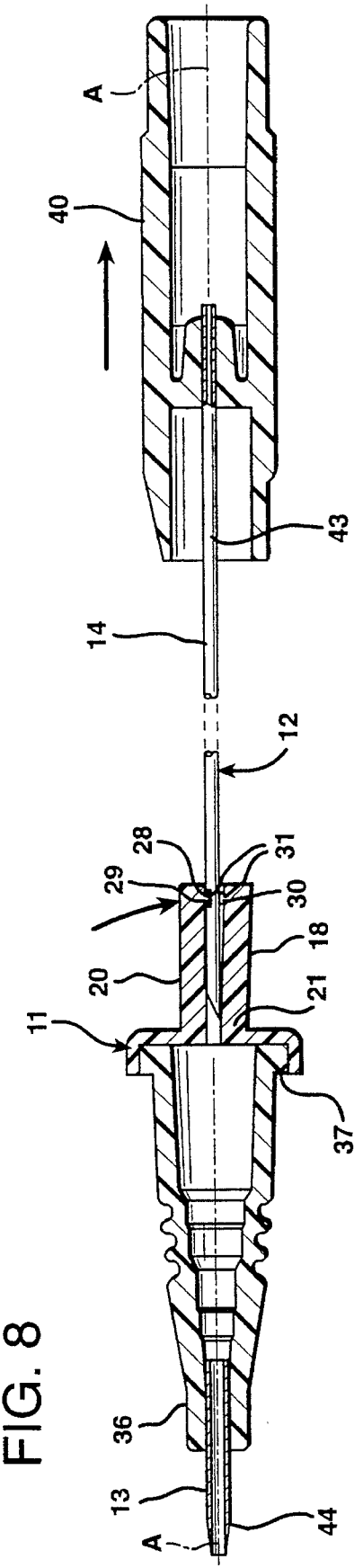
FIG. 8 is a view of the needle tip cover of FIG. 4 shown in cross section as in FIGS. 6 and 7 except the needle is shown mostly withdrawn from the catheter.

FIGS. 1 and 5 are side views of a catheter assembly 10 with a needle tip cover 11 wherein a needle 12 is fully seated within a catheter 13 of the catheter assembly 10. The needle 12 has an elongate shank 14 relative to an axis "A" thereof. The needle 12, preferably made of metal such as medical grade stainless steel, has a tip 15 at its distal axial end 16 terminating with a sharpened point 17. A cover 11 is coaxially associated with the elongate shank 14 for sliding movement therealong toward the tip 15. The cover 11 is most preferably made of a polymer and includes a part which extends 18 being parallel to the axis "A" to reach beyond the sharpened point 17 when the cover 11 is positioned near the tip 15. FIGS. 4 and 8 show the sharpened point 17 surrounded within the part which extends 18 to protect against accidental injury of the user. Alternatively, and as will be explained in detail the cover 11 shown in FIGS. 9 through 16 includes a hooked end 19 on the part which extends 18.

A lock 20 is operatively associated with the needle 12 and the cover 11 for cooperation therebetween to hold the cover 11 in position over the tip in ways to be described. Specifically, the lock 20 is for securing the cover 11 to prevent the cover 11 from axial movement relative to the needle tip 15 after positioning the cover 11 near the tip 15. In particular, the lock 20 prevents the cover 11 from being removed from the elongate shank 14.

Figure 9:
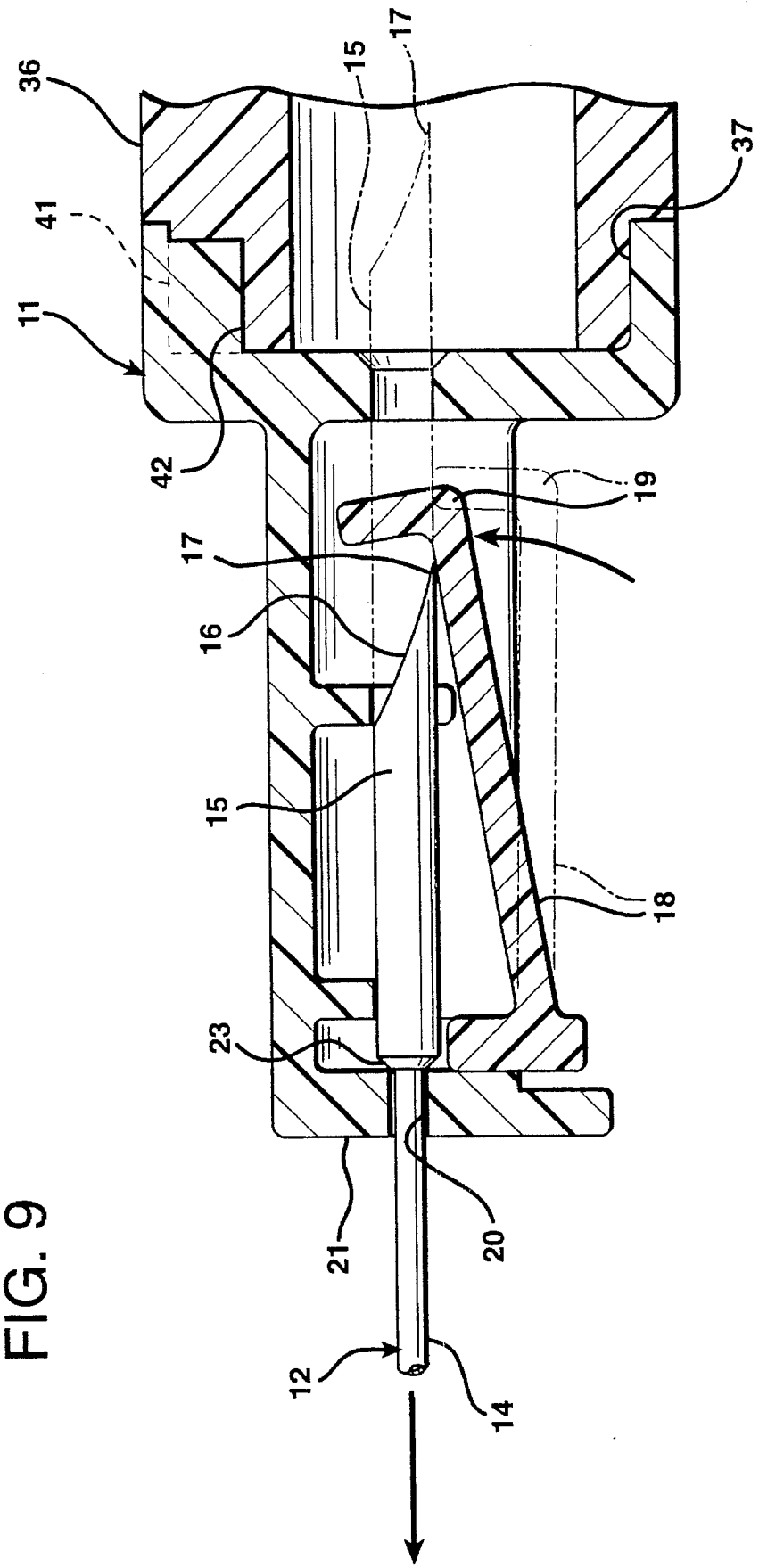
FIG. 9 is an enlarged side view in partial cross section of the cover; the needle tip and a portion of the elongate shank are locked in the cover by the part which extends and one form of the change in contour between the enlarged tip and a reduced diameter elongate shank.
Figure 10:
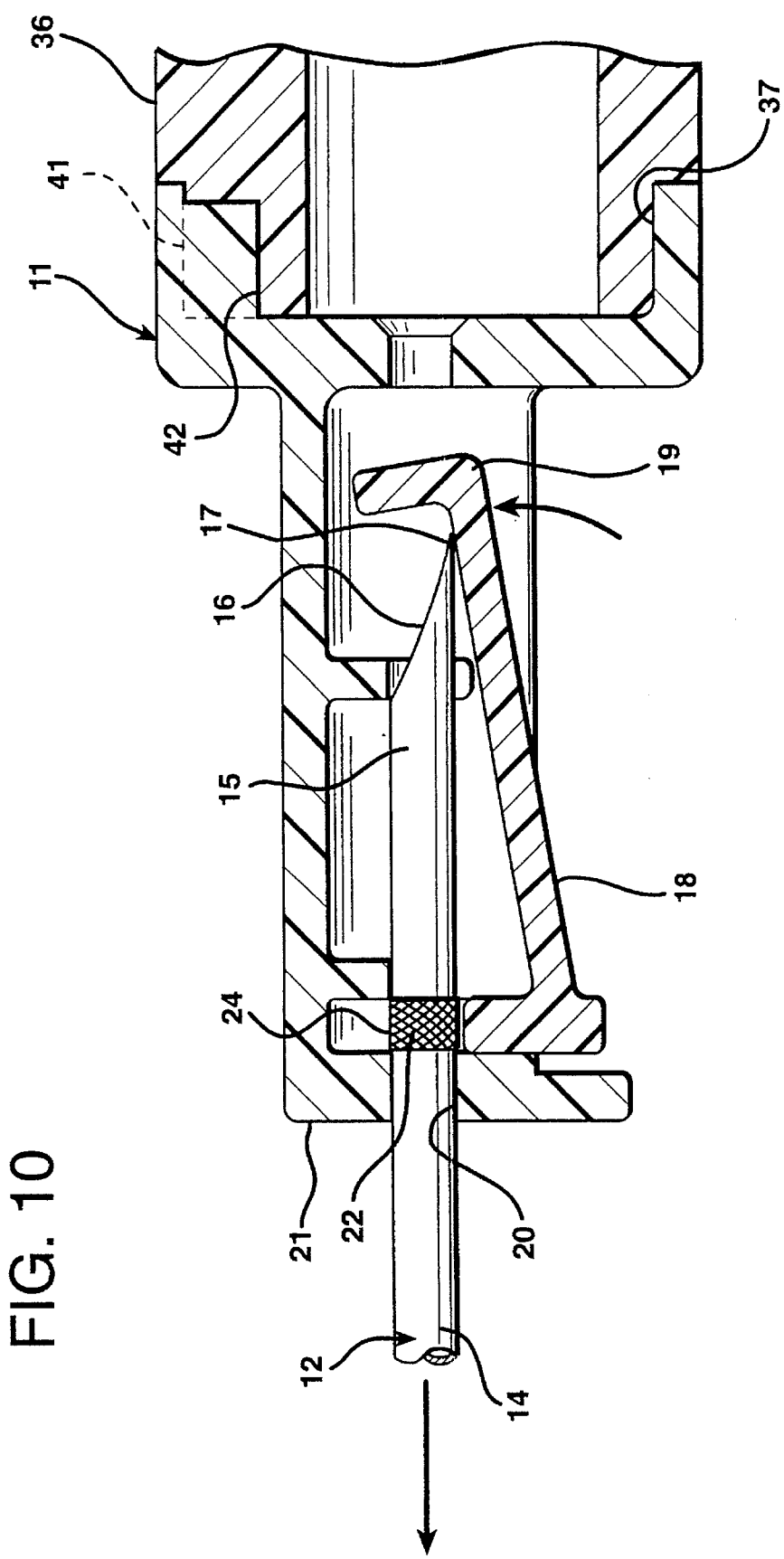
FIG. 10 is an enlarged side view partially in cross section of the cover wherein another form of the change in contour between the elongate shank and the tip is shown as a roughened surface such as by sandblasting or knurling.

The cover 11 has a bearing 21 for circumscribing and coaxial sliding on the elongate shank 14 and the part which extends 18 hangs cantilever from the bearing 21. Depending upon whether the cover 11, as shown in FIGS. 1 through 8 or as shown in FIGS. 9 through 15, is considered the part which extends 18 may be proximal or distal, respectively. The lock 20 includes a change in contour 22 of the needle 12 where the elongate shank 14 joins the tip 15 so that when the cover 11 interengages with the change in contour 22 further distal movement of the cover 11 is prevented. The change of contour 22 may be a transition 23 between a reduced diameter elongate shank 14 and an enlarged diameter on the tip 15 as illustrated in FIG. 9. The change in contour 22 may alternately be a roughened surface 24 on the needle 12 as depicted in FIG. 10. As shown in FIG. 10 the bearing 21 engages with the roughened surface 24 causing the bearing 21 to lock therewith preventing further axial movement since the cover 11 is of a relatively soft polymer and the roughened surface 24 is harder and has a coarse metallic surface.

Figure 11:
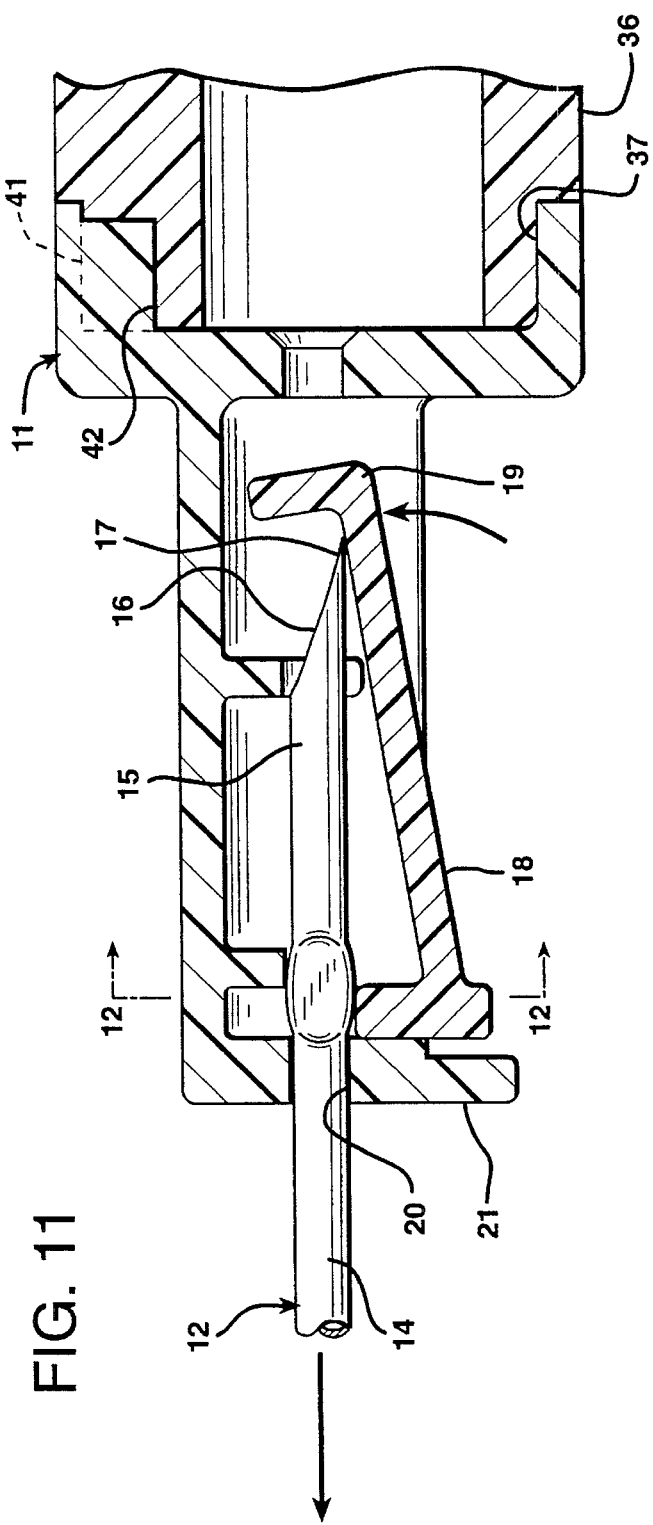
FIG. 11 is an enlarged side view partially in cross section of the cover wherein the elongate shank has a circular shaped cross section and an alternate form of the change in contour is shown as an oval or elliptical shaped cross section for the tip.
Figure 12:
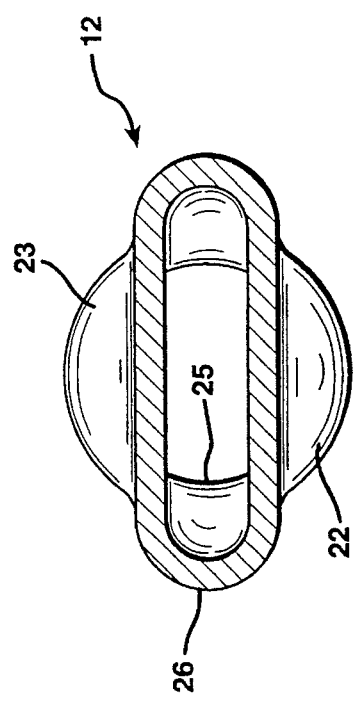
FIG. 12 is a view in cross section, taken along line 12—12 of FIG. 11, showing the change in contour between the elongate shank and tip.
Figure 13:
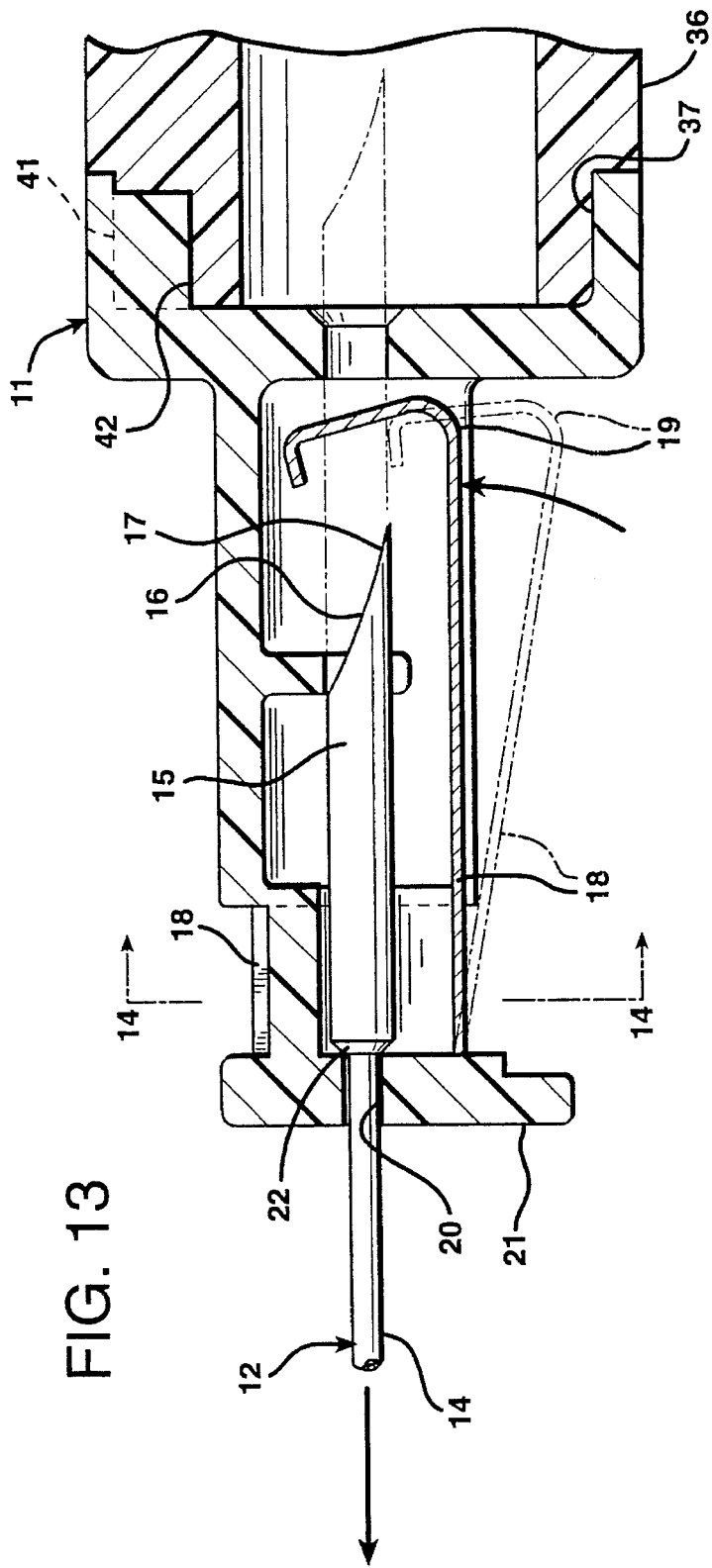
FIG. 13 is an enlarged side view partially in cross section of the cover showing the needle tip locked in the cover between the change in contour at the juncture of the enlarged tip and reduced diameter of the elongated shank and the part which extends is a resilient metal spring.
Figure 14:
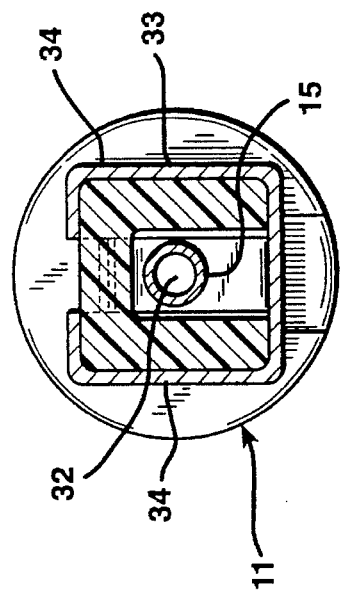
FIG. 14 is a view in cross section, taken along line 14—14 of FIG. 13, showing the metal spring retained on the tip cover.

In FIG. 12 the needle 12 is shown with a circular cross section 25 so that the change of contour 22 leads to a non-circular cross section 26 near the tip 15. It should be appreciated that while a specific change in contour 22 is shown and described herein, any change in contour including combinations of those disclosed should be considered equivalents. Specifically, FIGS. 11 and 12 include the circular cross section elongate shank 14 and a oval or elliptical cross section for the tip 15 but just pinching the tip 15 to effect the change could be an alternative.

In addition, FIGS. 2 through 4 and 6 through 8 include yet another alternate of the change of contour 22. A notch 28, cut into the needle 12, provides a latch face 29 and a pawl 30 on the cover which engages with the notch 28 at the latch face 29 and resists axial movement of the cover 11 proximally along the needle 12. The pawl 30 extends proximally from the bearing 21 and is resiliently supported thereon and is urged toward the elongate shank 14 so that the alignment of the pawl 30 with the notch 28 will cause interengagement thereby preventing further movement of the cover 11. The particular arrangements shown in FIGS. 2 through 4 and 6 through 8 have a pair 31 of opposed pawls 30 to seat in the notch 28 of the needle 12. The needle 12 may have a bore 32 therethrough along the axis "A" thereof if that is desired for the particular application of the catheter assembly 10.

Alternatively, the part which extends 18 may be primarily distal and the bearing 21 can be proximal, as shown in FIGS. 9 through 11. To prevent the proximal axial movement of the cover 11 away from the tip 15 on the elongate shank 14 after the cover 11 is positioned near the tip 15, the bearing 21 fits about the elongate shank 14 allowing sliding engagement and limiting distal axial movement of the cover 11 for preventing removal of the cover 11 from the elongate shank 14. The bearing 21 has an inside diameter to fit about the elongate shank 14 for controlling sliding axial movement therealong toward the change in contour 22.

The needle tip cover 11 of FIGS. 9 through 11 is a molded piece such as a highly resilient polymer material in order to provide the resilience necessary to protect the needle tip 15 as shown. The tip cover 11, however, should withstand high temperatures, sterilization and long periods wherein the part which extends 18 is held with its hooked end 19 in a ready to close position. In FIGS. 9 through 11 and 13 the part which extends 18 is shown with the hooked end 19 protecting the sharpened point 17.

To avoid problems of permanent set or distortion of a polymeric cover 11 due to maintenance in that ready to close position of the part which extends 18, an alternate approach is disclosed in FIGS. 13 through 16 wherein the resilience is provided by making the part which extends 18 of metal such as high strength medical grade stainless spring steel. The exact configuration of the metal part which extends 18 is shown in FIG. 15 and includes the hooked end 19 and a retainer portion 33. The part which extends 18 made of metal is, as in the all polymer cover 11 of FIGS. 9 through 11, a cantilever with a hooked end 19 and the retainer portion 33 has a pair of extended wrap around members 34 connected transversely to the end thereof opposite the hooked end 19. Members 34 cooperate with the molded polymeric tip cover 11 shown in FIG. 15 wherein the members 34 are spread apart, placed about and engaged with a square section 35 of the molded tip cover 11 shown in FIG. 14. An additional view which illustrates the relationship is the partial cross section shown in FIG. 13. The needle tip cover 11 design is not to be limited to the two arrangements shown, these are merely for purposes of illustration and are not to be considered limiting.

The catheter assembly 10 is of an over the needle type wherein a catheter 13 is inserted into a vessel by a single hand technique as described in U.S. Pat. No. 3,714,945. The catheter assembly 10, shown in FIGS. 2 through 4, 6 through 11, 13 and 15, has the cover 11 engaged about the outside of a catheter adapter 36 that is connected in fluid tight communication with the catheter 13. In FIGS. 2 through 4, 6 through 11, 13 and 15, the tip cover 11 is distally cupped for engagement with the proximal end of the catheter adapter 36. More particularly, a proximal external surface 37 of the catheter adapter 36 is a press fit with the distally cupped cover 11 in all but the arrangement of FIGS. 1 through 4 wherein the catheter adapter 36 has a luer thread 38 on its external proximal surface. The cover 11 has a distally extending internally threaded collar 39 located and shaped to conjugate in a threaded connection with luer thread 38. The press fit engagement of the cover 11 and the adapter 36 shown in FIGS. 6 through 8, 9 through 11 and 13 is such that the adapter 36 will retain and pull the cover 11 distally along the elongate shank 14 toward the change in contour 22 as the adapter 36 is separated from a needle hub 40. FIGS. 3 and 7 illustrate the separation of the hub 40 and the cover 11 and it should be appreciated that the various arrangements shown and described all separate in the same way whether the threaded engagement or the friction engagement is used. The separation of the adapter 36 and the hub 38 causes the cover 11 to slide distally on the elongate shank 14 of the needle 12 toward the change in contour 22.

There is a lug 41 on the proximal end of the cover 11 as shown in FIGS. 9 through 11 and 13, the lug 41 is arranged to engage with a groove 42 in the catheter adapter 36 such that the relative rotary relationship therebetween is maintained when the tip cover 11 is assembled with the catheter adapter 36. It will also be noted that the cover 11 has its cupped shape designed to close the proximal open of the catheter adapter 36 thereby retaining any blood or bodily fluids obtained during flashback.

A method of assembly of the needle hub 40 and the cover 11 to an end 43 opposite the tip 15 of the needle 12 and the needle 12 having the change in contour 22 and the cover 11 having the bearing 21 for circumscribing and coaxial sliding on the elongate shank 14, includes the following steps:

placing the cover 11 coaxially about the elongate shank 14 with the bearing 21 thereof axially slidable therealong, and securing the hub 40 to the end 43 in FIGS. 3, 4, 7 and 8 of the elongate shank 14 over which the bearing 21 was placed upon the needle 12 thereby capturing the cover 11 between the change in contour 22 and the hub 40.

A method of inserting the catheter assembly 10 by an over the needle technique requires the needle 12 and the cover 11 carried about the needle 12 on the elongate shank 14 thereof for movement therealong from the hub 38 to the tip 15, includes the following steps:

applying pressure to the catheter assembly 10 to penetrate the skin of an animal with the tip 15 of the needle 12 and carry a distal part 44 of the coaxially positioned catheter 13 into the skin;

inserting the catheter assembly 10 further through the skin of the animal by holding the hub 38 thereof between a finger and the thumb of the user, and moving the cover 11 axially along the needle 12 from the hub 40 to the tip 15 with another finger while withdrawing the hub 40 and needle 12 from the inserted catheter 13 and adapter 36 with the other finger and thumb to lock the cover 11 over the tip 15.

We claim:

1. A catheter introducer set, comprising:

a catheter adapter having a distal end and a proximal end with an external surface;

a cannula secured to the distal end of the catheter adapter;

a needle hub having a proximal end and an open distal end;

a needle having a sharp distal end and a proximal end secured to the needle hub, the needle being coaxially disposed within the open distal end of the needle hub and the cannula and having a change of contour therealong; and a needle cover coaxially disposed about the needle and disposed between the needle hub and the proximal end of the catheter adapter and having a distal end engaging the external surface of the proximal end of the catheter adapter to maintain the needle cover in engagement with the catheter adapter and a proximal end disposed within the open distal end of the needle hub and wherein the proximal end of the needle cover engages the change in contour along the needle to obstruct the sharp distal end of the needle when the sharp distal end of the needle is withdrawn into the needle cover.

2. The catheter introducer set of claim 1 wherein the change in contour along the needle is a notch.

3. The catheter introducer set of claim 1 wherein the change in contour along the needle is a non-circular cross-section.

4. The catheter introducer set of claim 1 wherein the change in contour along the needle is a transition between a reduced diameter and an increased diameter.

5. The catheter introducer set of claim 1 wherein the change in contour in the needle is a roughened surface on the needle.

* * * * *